United States Patent
Amanatullah

(10) Patent No.: US 9,468,570 B2
(45) Date of Patent: Oct. 18, 2016

(54) COOL CUT CAST SAW BLADE

(71) Applicant: Derek Amanatullah, Palo Alto, CA (US)

(72) Inventor: Derek Amanatullah, Palo Alto, CA (US)

(*) Notice: Subject to any disclaimer, the term of this patent is extended or adjusted under 35 U.S.C. 154(b) by 241 days.

(21) Appl. No.: 14/102,403

(22) Filed: Dec. 10, 2013

(65) Prior Publication Data

US 2015/0157515 A1    Jun. 11, 2015

(51) Int. Cl.
*A61F 15/02* (2006.01)

(52) U.S. Cl.
CPC .............. *A61F 15/02* (2013.01); *Y10T 83/04* (2015.04); *Y10T 83/293* (2015.04)

(58) Field of Classification Search
CPC ...... A61F 15/02; Y10T 83/293; Y10T 83/04
USPC .................... 83/835; 30/390, 373, 167, 287; 606/138, 176, 180, 172
See application file for complete search history.

(56) References Cited

U.S. PATENT DOCUMENTS

| | | | | |
|---|---|---|---|---|
| 3,786,814 A | * | 1/1974 | Armao | A61B 18/02 604/113 |
| 4,185,632 A | * | 1/1980 | Shaw | A61B 18/08 219/233 |
| 4,333,371 A | * | 6/1982 | Matsuda | B23D 59/025 83/169 |
| 4,568,830 A | * | 2/1986 | Stromswold | G01V 5/06 250/261 |
| 5,020,226 A | * | 6/1991 | Chabbert | A61F 15/02 30/373 |
| 5,702,415 A | * | 12/1997 | Matthai | A61B 17/14 30/339 |
| 6,379,371 B1 | * | 4/2002 | Novak | A61B 17/320068 30/123.3 |
| 6,925,917 B2 | * | 8/2005 | Tilley | B23D 45/003 30/123.3 |
| 2013/0269498 A1 | * | 10/2013 | Loukus | B23D 61/028 83/676 |

FOREIGN PATENT DOCUMENTS

GB            851306 A  * 10/1960  ............ F01D 5/081

* cited by examiner

*Primary Examiner* — Ghassem Alie
(74) *Attorney, Agent, or Firm* — Knobbe, Martens, Olson & Bear, LLP

(57) ABSTRACT

The present invention is a device and method for manufacturing such a device which is a significant and non-obvious improvement over previous methods of removing plaster or fiberglass casts used for medical treatment. Current cast saw blades create enough heat through friction to burn patients upon the removal of a plaster of fiberglass cast. This device is an improved cast saw blade design which substantially reduces the risk of thermal burns to patients during the process of removing plaster or fiberglass medical casts. The present invention includes a saw blade design which inhibits a rise in the surface temperature of the cast saw blade during use by using a core material (i.e., Gallium) within the blade, the core material having a lower melting temperature than the blade material, as a heat sink.

13 Claims, 4 Drawing Sheets

Isometric View – Cool-Cut Cast Saw Blade

Isometric View – Cool-Cut Cast Saw Blade

Top View - Serrated Cover

Bottom View - Serrated Cover

Top View - Bottom Dish**

A)

B)

COOL CUT CAST SAW BLADE

CROSS-REFERENCE TO RELATED APPLICATIONS

No provisional patent has been sought for this invention. This application claims priority of European Patent Office as well as the United States Patent Office. No separate patent application has been filed with the European Patent Office. Also, no other prior art is substantially similar to this invention. Though the cast saw is an article of common use in the medical field today, no invention has been widely accepted which fixes the problem of thermal burns to patients who have their casts removed by cast saw.

STATEMENT REGARDING FEDERALLY SPONSORED RESEARCH OR DEVELOPMENT

This application was developed through private funding. Absent a subsequent agreement with the Federal Government the named inventor does not abdicate any rights to this patent to the Federal Government.

PARTIES TO A JOINT RESEARCH AGREEMENT

Not Applicable.

SEQUENCE LISTING

Not Applicable.

INCORPORATION-BY-REFERENCE OF MATERIAL SUBMITTED ON A COMPACT DISC

Not Applicable.

BACKGROUND OF INVENTION

1. Field of Invention

The present invention is a non-obvious improvement to a medical device called a cast saw. A cast saw is a medical device used to cut through a plaster or fiberglass cast. The invention is an improved blade for a cast saw that replicates the cutting ability of traditional cast saw blade and reduces the surface temperature of the cast saw blade.

2. Description of Related Art

The oscillating cast saw is a tool of common usage in the medical community for removing plaster and fiberglass casts. One embodiment of an oscillating cast saw is described in U.S. Pat. No. 5,878,607. An earlier embodiment of the cast saw is described in U.S. Pat. No. 4,412,381.

The cool cast saw blade is an improvement on the existing oscillating cast saw devices as described in U.S. patents such as U.S. Pat. Nos. 5,878,607 and 4,412,381. However, other devices have been previously patented which improve certain aspects of the cast saw. Other devices that seek to minimize or eliminate the risk of thermal burns to patients who have their casts removed by oscillating cast saws exist. One such invention is discussed in U.S. Pat. No. 5,944,675, which discloses a protective shield which would shield patients from a burn from an oscillating cast saw. U.S. Pat. Nos. 4,411,067 and 4,316,323 discloses a blade housing for a type of cast saw. Other patents such as U.S. Pat. No. 4,227,517 embody different cast cutting systems.

General Description

A cast saw is a mechanical device which uses oscillating motions of a circular saw blade to cut through a plaster or fiberglass medical cast. Cast saws are used frequently by physicians and physician extenders (assistants). This invention reduces or cures the problem of cast saws causing thermal burns to patients. This is a major problem with existing cast saw mechanical devices. All traditional cast saw blades heat through friction when cutting through plaster of fiberglass medical casts. The friction between the metal blade and the plaster or fiberglass being cut creates enough heat to burn patients. Cast saw burns currently occur at a rate of approximately 1 burn for every 1,000 patients. Children and sedated patients have a higher risk of cast saw burns because these patients cannot effectively verbalize pain. In addition, no educational, regulatory, or administrative stipulations have been able to eliminate cast saw burns.

BRIEF SUMMARY OF THE INVENTION

This invention is non-obvious because no invention reducing thermal burns to patients has yet gained widespread acceptance by the medical community. The need for a popular cast saw mechanical device which reduces or eliminates thermal burns of patients is clear; and no such invention has yet gained widespread acceptance by the medical community. The Leapfrog Group, a group which promotes improvements in the safety of health care, defined a "Never Event" as "adverse events that are serious, largely preventable, and of concern to both the public and health care providers for the purpose of public accountability." "Disability associated with a burn incurred from any source while being cared for in a healthcare facility" is one of 28 National Quality Forum recognized "Never Events". Any technology that would prevent or eliminate cast saw burns would become the standard of care for liability and patient safely concerns.

Other inventions and applications which would reduce patient thermal burns by cast saws have failed to gain widespread acceptance in the medical community. Thermal resistant cast padding and the Zip Stick are two inventions which have been proposed to protect patients from cast saw burn. These technologies require direct application when making and removing each cast. A more passive technology that does not require specific application during cast application or removal would be more easily accepted, and applied by the medical community. The cool-cut cast saw blade reduces the surface temperature of the cast saw blade by using a low melting point core material (e.g., Gallium) within the blade as a heat sink. The cool-cut cast saw blade does not alter the form or function of the cast saw itself; it simply replaces a traditional cast saw blade with a cool-cut cast saw blade that is similar in dimensions and form to traditional cast saw blades.

The claimed invention includes both a device and the method of manufacture for this device. The device is named the cool cast saw blade. The cool cast saw blade is an assembly of materials which reduce the possibility of medical patient being burned during the removal of plaster or fiberglass casts from high temperature of a cast saw blade which currently still occur. Modern cast saw blades heat up through friction and are unable to disburse this heat. As a result the cast saw blades become so hot that they can burn patients. The cool cast saw blade better absorbs the heat created by the friction than current cast saw blades.

The cool-cut cast saw blade reduces the surface temperature of the cast saw blade by using a low melting point core material within the blade as a heat sink. Since the heat on the surface is disbursed to the core of blade, the surface is cooler and there is less of a chance of burns for the patients. All materials absorb energy when they are heated. When materials melt they remain at a constant temperature while undergoing the phase change (e.g., from a solid to a liquid). The energy (Q) absorbed by a material is defined by the mass of the material (m), the change ($\Delta$) in temperature (T), and the heat capacity of the material (c), $Q=mc\Delta T$. The energy to melt (i.e., energy of fusion) a material is defined by the mass of the material and the heat of fusion for that material ($\Delta H_{fusion}$), $Q=m\Delta H_{fusion}$. Hence, any low melting point material may be used a heat sink for another higher melting point material. When the temperature reaches the melting point of the low melting point material it will absorb energy but remain at a constant temperature while making the phase transition from a solid to a liquid. This effect will slow the heating of (a.k.a., cool or act as a heat sink for) the higher melting point material. These material properties can be applied to solve the issue of temperature elevation with cast saw blade friction that results in cast saw burns. This device, in contrast to previous devices, allows for the absorption of heat and thus reduces the chance of burns to patients during the cast removal process. This device will consist of two solid components made of tungsten carbide which fit together to enclose gallium which can be in solid or liquid state. Gallium as a material will be discussed first in relation to its use in this device, followed by tungsten carbide.

Metallic Gallium is not considered toxic. Prolonged exposure may cause dermatitis. Soluble gallium salts tend to form an insoluble hydroxide when injected in large amounts. In animals this results in renal toxicity. In lower doses, soluble Gallium is tolerated well, and does not accumulate. Gallium specifically has no known role in biology, however it can mimic iron. Gallium can replace the redox activity of iron and interfere with the transfer of electrons required for metabolic respiration. Gallium is currently used as an amalgam for dental reconstruction, a pharmaceuticals (i.e., Gallium nitrate/Ganite, Gallium maltolate, MR045), and a radiopharmaceuticals (Gallium citrate GA 67).

Liquid metals wet solid metal surfaces. Room-temperature Gallium can be reactive with certain metals, except tungsten and tantalum which have a high resistance to corrosion. Tungsten has the highest melting point (3,422° C., 6,192° F.) and tensile strength (344.8 MPa) of all metals. Tungsten is used in the production of hard materials based on Tungsten carbide, one of the hardest carbides, with a melting point of 2770° C. Tungsten carbide is an efficient electrical conductor. Tungsten carbide is currently used to make wear-resistant abrasives and cutters and knives, for drills, circular saws, milling and turning tools. Tungsten is the heaviest element known to be biologically functional in some bacteria, but not in eukaryotes (e.g., humans).

The typical mass of a modern cast saw blade is approximately 10 grams. Since the density of Stainless Steel is approximately 8.03 g/cc (grams per cubic centimeter) then a traditional cast saw blade has 1.25 cc of Stainless Steel. 1 cc of the volume of the cast saw blade at its core is replaced with 5.73 g of Gallium (a.k.a., the low melting point material). The remaining 0.25 cc on the outer surface of cast saw blade is replaced with 4.30 g Tungsten carbide (a.k.a., the high melting point material). The cool-cut cast saw blade does not alter the form, function, or dimension of a traditional cast saw blade; it simply replaces traditional cast saw blade materials with cool-cut cast saw blade materials (i.e., a low melting point material at the core of a high melting point material).

A traditional cast saw blade increases in temperature from room temperature (25° C., 77° F.) to 105° C. well above the temperature required to burn human skin; this requires 400 J (Joules). As a cool-cut cast saw blade (e.g., Tungsten carbide blade with a Gallium core) absorbs this 400 J of energy, the Gallium core heats from room temperature to its melting point (29.771° C., 85.588° F.) absorbing 10 J of energy. As the 5.73 g of Gallium in the core begins to melt it remains at it melting point absorbing 489.877 J of energy before melting all of the 5.73 g of Gallium and allowing the temperature of the cool-cut cast saw blade to rise above the melting point of the Gallium core. The Tungsten Carbide skin gives its energy and heat to the Gallium core, reducing the overall temperature of the cool-cut cast saw blade. The low melting point material core is a heat sink for the high melting point material skin reducing the surface temperature of the cool-cut cast saw blade compared to any traditional cast saw blade.

The manufacturing of the cool-cut cast saw blade includes but is not limited to machining the high melting point surface material to be filled with the low melting point core material. Gallium expands by a factor of 0.031 when it undergoes a phase change from solid to liquid. Hence, manufacturing of the cool-cut blade is best conducted with gallium in the liquid phase to prevent rupture of the surface material when the contained Gallium expands as it melts. Any process that coats a low melting point solid core material with a high melting point surface material for the purpose of cutting would also constitute making a cool-cut cast saw blade as a low melting point material is used as a heat skin for the high melting point outer surface in its final application.

A tungsten carbide dish is manufactured with the capacity to hold 1 cc of liquid Gallium (FIG. 4). This dish will hold the liquid Gallium. Next, a Tungsten carbide blade is manufactured that mates to the dish and traps the liquid Gallium in core of the cool-cut cast saw blade and provides the teeth of the cool-cut cast saw blade (FIG. 2 and FIG. 3). The liquid Gallium is poured into the Tungsten carbide dish and then mated with the Tungsten carbide blade. A small amount of alcohol may be required to efficiently pour the 1 cc of liquid Gallium into the dish. The alcohol is evaporated prior to vacuum brazing above 800° C. but below the boiling point of Gallium (2,205° C., 4,001° F.) to fuse the Tungsten carbide dish and blade components and trap the gallium core in the final assembled form of the cool-cut cast saw blade. Brazing or other processes may be used to apply surface coatings to the assembled cool-cut cast saw blade to provide an additional seal or a visual wear or thermal indicators.

BRIEF DESCRIPTION OF THE SEVERAL VIEWS OF THE DRAWING

Further features, properties and advantages of the present invention will become clear from the following description of embodiments in conjunction with the accompanying drawings. The described features are advantages alone and in combination with each other.

This device is meant to be simple and easily manufactured.

Figure 2:
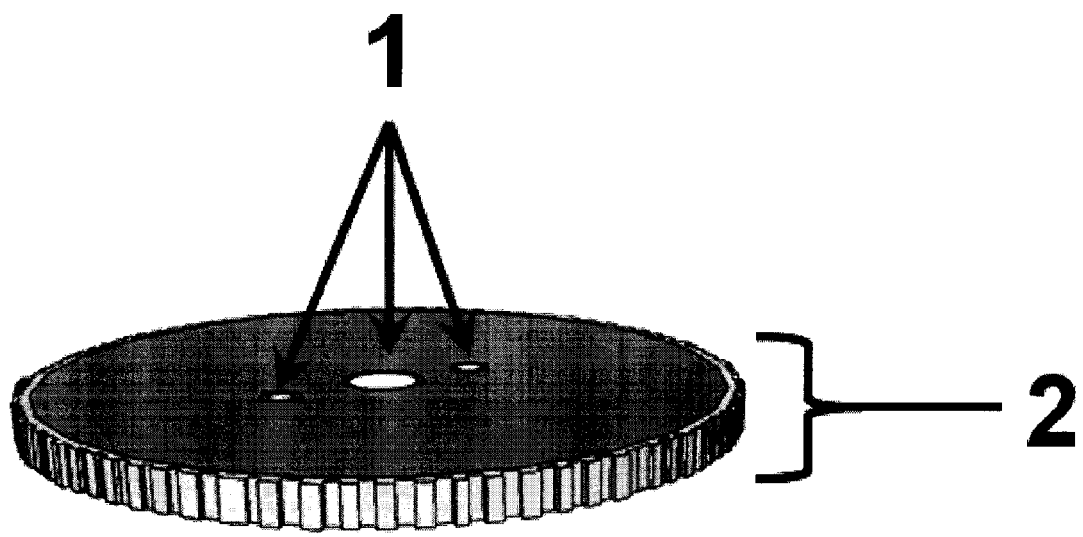
FIG. 2 shows a top perspective view of a serrated cover of one embodiment of a blade assembly.
Figure 3:
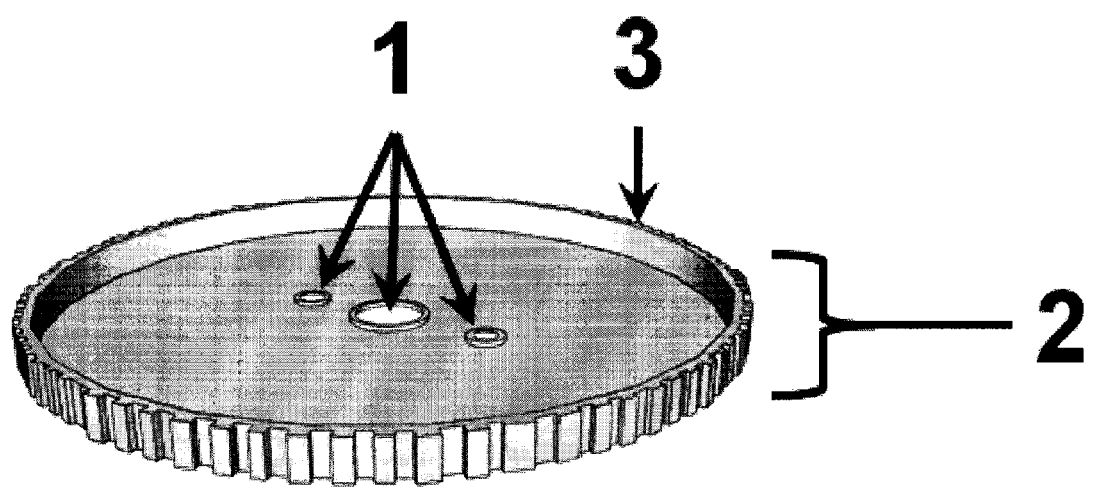
FIG. 3 shows a bottom perspective view of the serrated cover FIG. 2.

The device assembles to trap a liquid in its core. The liquid is held in the bottom dish (FIG. 4) and the serrated cover completely encases the bottom dish entrapping the liquid core and exposing the serrated edges of the serrated cover (FIG. 2 and FIG. 3).

DETAILED DESCRIPTION OF THE INVENTION

This device consists of three components. The assembly process is described below. First is a "bottom dish", made of tungsten carbide or similar material, with holes machined to fit into a cast saw assembly and including any necessary structural supports. Second, and inside that bottom dish, "liquid" Gallium is poured into the dish. Third, a "serrated cover" made of tungsten carbide or similar material will fit over the dish and seal in the gallium as well as contain holes machined to fit into a cast saw assembly, including any necessary structural supports, and a serrated outer edge or blade used to cut a fiberglass or plaster cast. The serrated cover will be fused to the bottom dish trapping the liquid inside. This entire completed assembly is known as the cool-cut cast saw blade. This device is meant to be used as the blade for a cast saw which works by vibrating or oscillating a cast saw blade to cut through a plaster or fiberglass cast, but its application is not limited to this indication as non-orthopedic applications may necessitate blade temperature regulation.

The cool-cut cast saw blade is intended to be used as a replacement for the current cast saw blades used in an orthopedic cast saw. Orthopedic cast saws use vibration rather than rotation of the blade to remove or cut the cast material applied to the patient's extremity. Currently orthopedic casts consist of a cotton, Gortex™, or other soft material wrapped over the limb of a patient. Over this padding, a fiberglass or plaster coating is added and cured to provide the stiffness that keeps the limb in appropriate alignment. A cast saw blade needs the resistance of a stiff material to cut. The padding and skin underneath the hard plaster or fiberglass cast will move with the vibration of the saw blade, allowing the blade to cut the hard plaster or fiberglass and spare the padding and skin. These same vibrations that cut the hard plaster and fiberglass cast generate the friction that heats traditional cast saw blades resulting in cast saw burns.

The medical device in question consists of three basic components shown in the figures.

Figure 1:
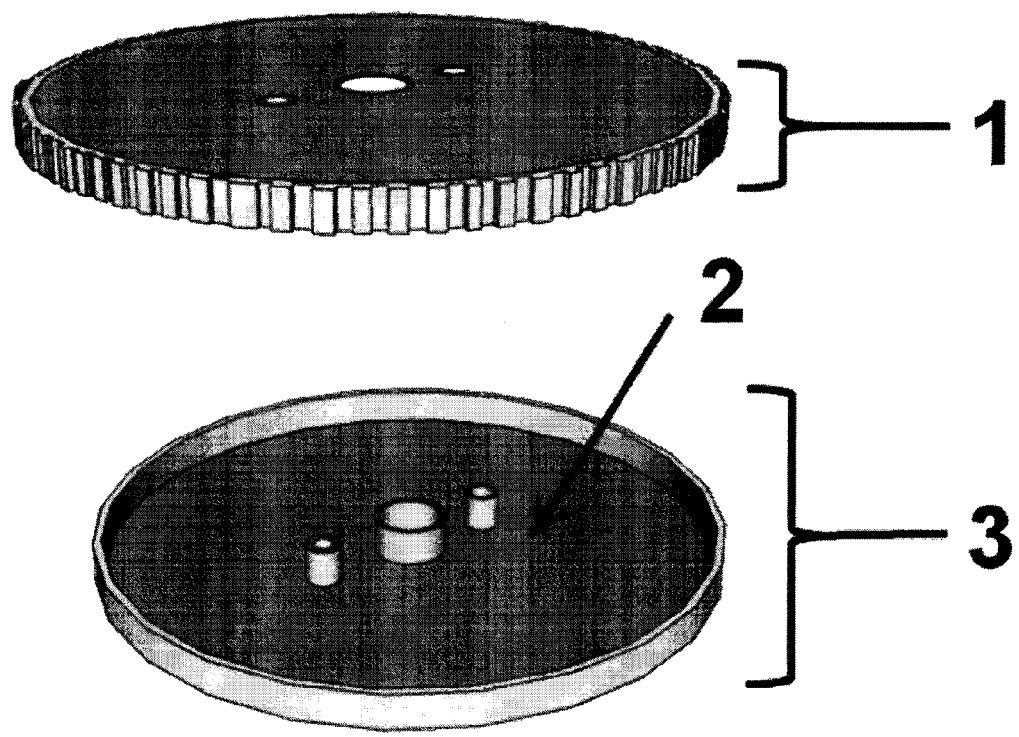
FIG. 1 shows an exploded perspective view of one embodiment of a blade assembly.

Component 1:

FIG. 1 (arabic numeral 1), FIG. 2, and FIG. 3 show the serrated cover. This serrated cover shall be referred to as Component 1. Component 1 will be made of Tungsten carbide or other similar high melting point material. Component 1 will contain one central hole and several other satellite holes. These holes can be arranged and sized to allow mounting of the assembled cool-cut cast saw blade to any oscillating cast saw. An oscillating cast saw is a mechanical device commonly used to remove plaster casts from medical patients with broken bones or other medical injuries. An oscillating cast saw will use this invention (cool cast saw blade) as a blade to oscillate, rapidly rotate in a clockwise and counterclockwise direction, to remove a plaster cast or other type of medical cast. Component 1 will contain a serrated edge that will allow cutting by oscillation. This serrated edge is shown in FIG. 2, numeral 2 and FIG. 3, numeral 2. Component 1 will contain a raised edge that will allow the bottom dish (see Component 2) to fit completely within Component 1 exposing the serrated edge and trapping the low melting point material when the serrated top and bottom dish are fused together. The top and bottom dish will be fused together by using welding or other similar process. This edge is shown in FIG. 3, numeral 3.

Figure 4:
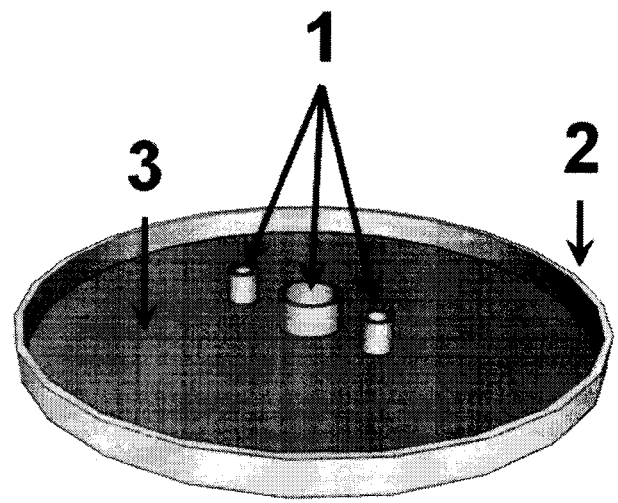
FIGS. 4A-B shows a top perspective view of the bottom dish A) empty and B) filled.
Figure 4:
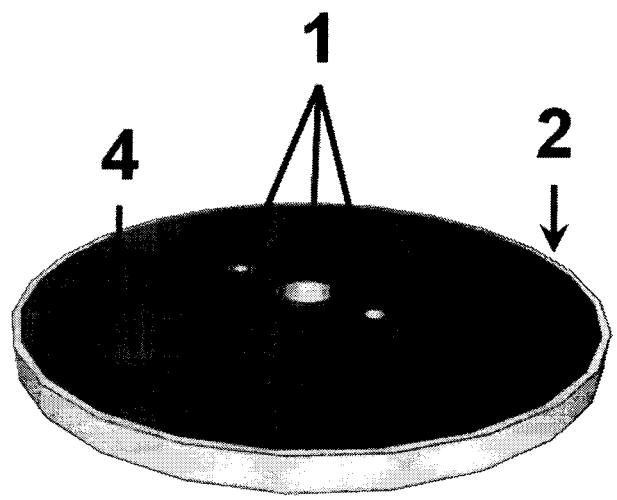

Component 2:

FIG. 1, numeral 3 and FIG. 4 show the bottom dish. This bottom dish shall be referred to as Component 2. Component 2 will be made of Tungsten carbide or other similar high melting point material. Component 2 will contain one central hole and several other satellite holes; these holes can be arranged and sized to allow mounting of the assembled cool-cut cast saw blade to any oscillating cast saw, FIG. 4—numeral 1. Component 2 will contain a raised edge that will allow the bottom dish to be filled with a low meting point material (see Component 3), FIG. 4—numeral 2.

Component 3:

Component 3 is the low melting point material, such as liquid gallium or similar material, placed into the void of Component 2, FIG. 4 numeral 3. Component 3 will be made of Gallium or other similar low melting point material. Component 3 is shown in FIG. 4—numeral 4. Component 3 will be completely enclosed in Components 1 and Component 2 once the device is fully assembled. This low melting point material will cool the serrated edge of Component 1 so as to not significantly burn the skin of a patient.

The invention claimed is:

1. A saw blade for a saw, comprising:
a cover of a first material having a first generally planar surface and a first raised edge with a serrated outer edge; and
a dish member of said first material having a second generally planar surface and a second raised edge, the cover configured to fit over and to be fused to the dish member to define a sealed chamber between the first and second generally planar surfaces configured to enclose and contain a volume of a second material different than the first material,
wherein the second material has a lower melting point temperature than the first material such that the volume of the second material transitions from a solid to a liquid and operates as a heat sink as the saw blade heats up during use, thereby inhibiting a rise in temperature of the first and second generally planar surfaces and the serrated outer edge while operating the saw.

2. The saw blade of claim 1, wherein the first material is Tungsten carbide.

3. The saw blade of claim 1, wherein the second material is Gallium.

4. The saw blade of claim 1, wherein the cover is configured to fit over the dish member such that dish member fits completely within the cover.

5. The saw blade of claim 1, wherein the saw is an orthopedic cast saw and wherein the first and second generally planar surfaces have one or more holes configured to allow coupling of the saw blade to the orthopedic cast saw.

6. The saw blade of claim 5, wherein the one or more holes comprise a central hole and one or more satellite holes.

7. A cutting member for a cutting tool, comprising:
a cutting edge defined at least partially along a periphery of the cutting member, a first planar surface spaced apart from a second planar surface to define a sealed chamber, the first and second planar surfaces and cutting edge made of a first material, said sealed chamber configured to enclose and contain a volume of a second material different than the first material, wherein the second material has a lower melting point temperature than the first material such that the volume of the second material transitions from a solid to a liquid and operates as a heat sink as the cutting member heats up during use.

8. The cutting member of claim 7, wherein the first material is Tungsten carbide.

9. The cutting member of claim 7, wherein the second material is Gallium.

10. The cutting member of claim 7, wherein the first planar surface at least partially defines a cover member and the second planar surface at least partially defines a dish member, the cover and dish member being coupleable to each other, the dish member having an inner surface and a circumferential wall that at least partially define the sealed chamber.

11. The cutting member of claim 10, wherein the cover member is configured to fit over the dish member such that dish member fits completely within the cover member.

12. The cutting member of claim 10, wherein the cover and dish member are welded together.

13. The cutting member of claim 7, wherein the cutting member is removably coupleable to the cutting tool.

* * * * *